(12) United States Patent
Flynn et al.

(10) Patent No.: US 11,150,217 B2
(45) Date of Patent: Oct. 19, 2021

(54) METHOD FOR DIRECTLY MEASURING SO2 AND OTHER TRACE GASES BY ELECTROCHEMICAL CELL (ECC) SONDE

(71) Applicant: University of Houston System, Houston, TX (US)

(72) Inventors: James Flynn, Magnolia, TX (US); Gary A. Morris, Austin, TX (US)

(73) Assignee: UNIVERSITY OF HOUSTON SYSTEM, Houston, TX (US)

( * ) Notice: Subject to any disclaimer, the term of this patent is extended or adjusted under 35 U.S.C. 154(b) by 210 days.

(21) Appl. No.: 16/493,721

(22) PCT Filed: Mar. 13, 2018

(86) PCT No.: PCT/US2018/022235
§ 371 (c)(1),
(2) Date: Sep. 12, 2019

(87) PCT Pub. No.: WO2018/169996
PCT Pub. Date: Sep. 20, 2018

(65) Prior Publication Data
US 2020/0011832 A1 Jan. 9, 2020

Related U.S. Application Data

(60) Provisional application No. 62/470,579, filed on Mar. 13, 2017.

(51) Int. Cl.
*G01N 27/49* (2006.01)
*G01N 27/413* (2006.01)
*G01N 27/403* (2006.01)
*G01N 33/00* (2006.01)
*G01N 27/416* (2006.01)

(52) U.S. Cl.
CPC .......... *G01N 27/49* (2013.01); *G01N 27/403* (2013.01); *G01N 27/413* (2013.01); *G01N 33/0042* (2013.01); *G01N 27/4162* (2013.01)

(58) Field of Classification Search
CPC .............. G01N 27/403; G01N 27/413; G01N 27/4162; G01N 27/49; G01N 33/0039; G01N 33/0042
See application file for complete search history.

(56) References Cited

U.S. PATENT DOCUMENTS

| | | | |
|---|---|---|---|
| 3,681,228 A | 2/1969 | Komhyr | |
| 3,855,096 A | * 12/1974 | Bergman | ............. G01N 27/404 204/412 |
| 4,250,737 A | 2/1981 | Biglin | |

(Continued)

OTHER PUBLICATIONS

"Reference Electrode" Technical Note on the ALS Co., Ltd. website https://www.als-japan.com/1647.html downloaded Jun. 4, 2021 (Year: 2021).*

(Continued)

Primary Examiner — Alexander S Noguerola
(74) Attorney, Agent, or Firm — Conley Rose, P.C.

(57) ABSTRACT

A method of directly measuring $SO_2$ and other trace gases by configuring an electrochemical cell (ECC) sonde; and an ECC sonde pump inlet filter to remove ozone and other trace gases. Further, calibration and operation procedures for the $SO_2$ and other trace gas ECC sondes are disclosed.

20 Claims, 9 Drawing Sheets

(56) References Cited

U.S. PATENT DOCUMENTS

| | | | |
|---|---|---|---|
| 5,117,680 A | 6/1992 | Colvin | |
| 5,474,665 A | 12/1995 | Friese et al. | |
| 2003/0155241 A1 | 8/2003 | Lai et al. | |
| 2005/0254851 A1 | 11/2005 | Kim et al. | |
| 2006/0159583 A1* | 7/2006 | Naslund | B65B 55/08 422/22 |

OTHER PUBLICATIONS

International Patent Application No. PCT/US2018/022235 International Search Report and Written Opinion dated May 24, 2018 (12 pages).

Morris et al., "A Balloon Sounding Technique for Measuring SO2 Plumes," Journal of Atmospheric and Oceanic Technology, Mar. 25, 2010, vol. 27, pp. 1318-1330.

Kanda et al., "Interference of Sulphur Dioxide on Balloon-borne Electrochemical Concentration Cell Ozone Sensors over the Mexico City Metropolitan Area," Asian Journal of Atmospheric Environment, Sep. 2014, vol. 8-3, pp. 162-174.

Schenkel et al., "Interference of Some Trace Gases with Ozone Measurements by the Ki Method," Atmospheric Environment, 1982, vol. 16, No. 9, pp. 2187-2190.

Komhyr, "Electrochemical concentration cells for gas analysis," Annales de Geophysique, 1969, t. 25, fasc. 1, pp. 203-210 (9 pages).

Smit, Herman G. J. et at., "Assessment of the Performance of ECC-Ozonesondes Under Quasi-Flight Conditions in the Environmental Simulation Chamber: Insights from the Juelich Ozone Sonde Intercomparison Experiment (JOSIE)," Journal of Geophysical Research, vol. 112, D19306, 2007 (18 p.).

* cited by examiner

METHOD FOR DIRECTLY MEASURING SO2 AND OTHER TRACE GASES BY ELECTROCHEMICAL CELL (ECC) SONDE

CROSS-REFERENCE TO RELATED APPLICATIONS

This application is a National Phase Entry of, and claims priority to PCT Application No. PCT/US2018/022235, filed Mar. 13, 2018 which claims priority to U.S. provisional application Ser. No. 62/470,579, filed Mar. 13, 2017, the entire contents of each hereby incorporated by reference herein for all purposes.

STATEMENT REGARDING SPONSORED RESEARCH

This invention was made with U.S. Government support under Grant No. NNG11HP16A, awarded by the National Aeronautics and Space Administration. The government has certain rights in the invention.

TECHNICAL FIELD

This disclosure relates to a method for directly measuring $SO_2$ and other trace gases by using an electrochemical cell (ECC) sonde. More particularly, this disclosure relates to a method for directly measuring $SO_2$ and other trace gases by using an electrochemical cell (ECC) sonde; and an ECC sonde pump inlet filter to remove ozone and other trace gases; and further discloses calibration and operation procedures for the $SO_2$ and other trace gas ECC sonde(s).

BACKGROUND $SO_2$ is an important atmospheric trace gas. When converted to sulfate aerosols, the resulting particles impact the radiative balance of the planet and have important implications for radiative transfer models and global climate change influences. $SO_2$ profile measurements are of value to the satellite data community, which require validation of satellite measurements, and are valuable for measuring plumes of $SO_2$ from coal-fired power plants, production facilities, and natural sources such as volcanic plumes.

Currently, all known methods of measuring $SO_2$ by ECC sonde require the concentration of ozone to be greater than Sulphur dioxide ($[O_3]>[SO_2]$) and for two ECC sondes to be flown on the same payload (Morris et al., 2010). In this "dual sonde" approach one ECC sonde uses an $SO_2$ filter on the inlet to selectively remove $SO_2$ and let $O_3$ pass to the cell unaffected, resulting in a measurement of $[O_3]$. The second ECC sonde is operated without a filter and measures $[O_3]-[SO_2]$, allowing the calculation of $[SO_2]$ in post processing via subtraction of the two signals. While this approach has been demonstrated effective in the troposphere (0-15 km), as $O_3$ concentrations increase rapidly above the tropopause, the technique is less effective. In particular, the dual sonde approach would have been unable to detect the lower stratospheric portion of the plume from the Mt. Pinatubo eruption (June 1991) for more than a day or two after the eruption, and as a result an alternate approach with higher sensitivity is required to be able to sample $SO_2$ in the lower stratosphere. Furthermore, in the presence of significant $SO_2$ concentrations associated with a volcanic emission, the dual sonde approach cannot measure $SO_2$ under conditions when $[O_3]<[SO_2]$.

Therefore, a method that provides a quantitative measurement of $SO_2$ independently of $O_3$ is greatly needed in the art. Such an approach would improve measurements throughout the profile, but in particular under conditions in the troposphere under which $[O_3]<[SO_2]$ and in the lower stratosphere, where the dual sonde approach is not sufficiently sensitive to report reliable measurements.

Further, aircraft that take or collect such samples are reluctant to fly into volcanic plumes before they have sufficiently dispersed because the ash can cause turbine engine failure, therefore a technique to directly sample such eruptions within the plume during the first week or two after the eruption is also in great need.

Thus, new methods of collecting and measuring $SO_2$ are sort in the field. As such, and disclosed herein are embodiments of new methods of collecting and measuring $SO_2$ thereby addressing such unmet needs in the field.

BRIEF DESCRIPTION OF THE DRAWINGS

For a more complete understanding of the present disclosure, reference will now be made to the accompanying drawings/figures in which.

SUMMARY OF THE DISCLOSURE

Figure 1:
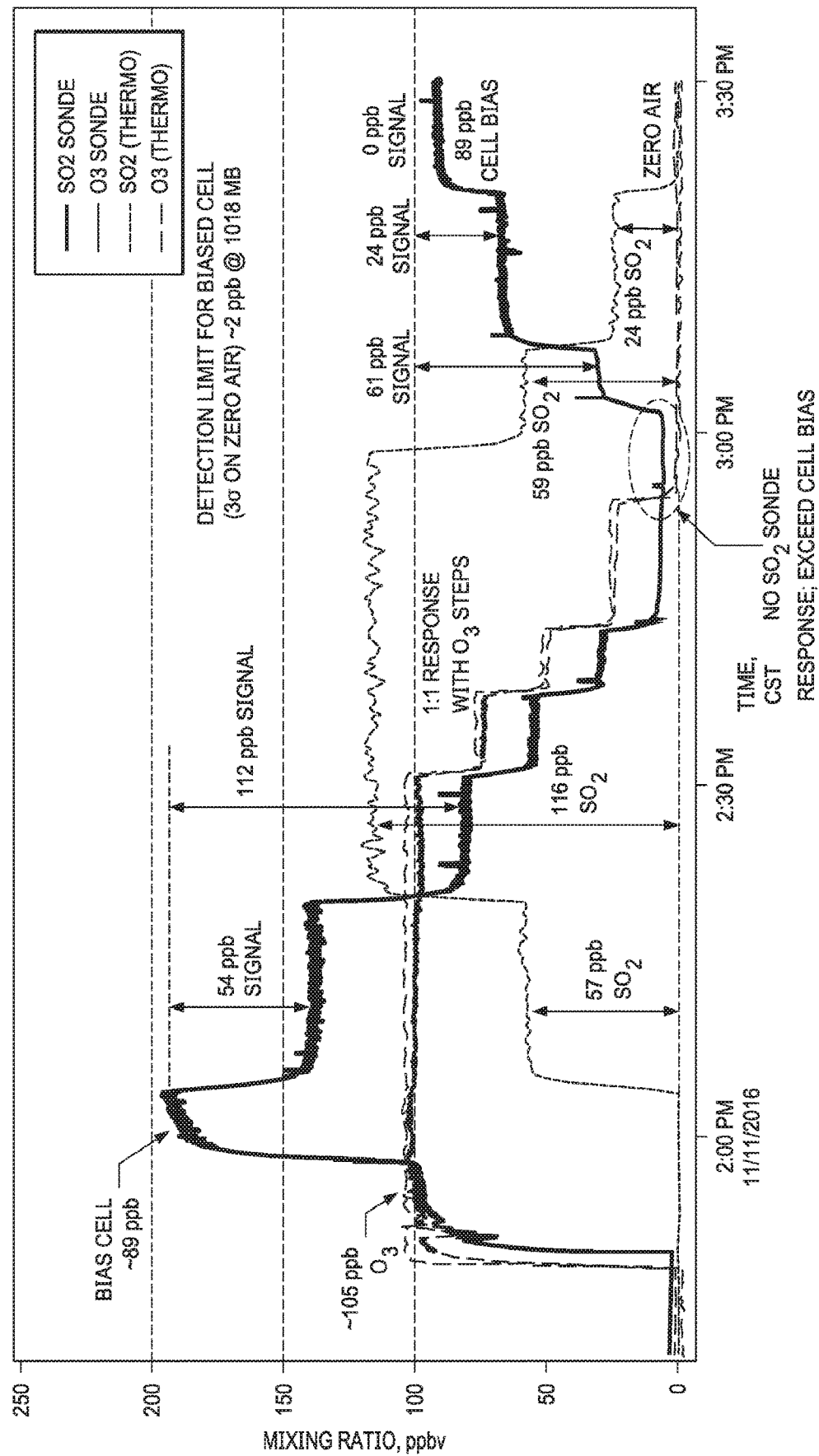
FIG. 1 illustrates an annotated time series demonstrating the cell bias method of measuring $[SO_2]>[O_3]$ with a single sonde.

Disclosed herein in some embodiments is a method of directly measuring $SO_2$ and other trace gases by inducing an electric current in a cell, and allowing the use of a single ECC sonde to quantitatively measure $SO_2$ without the limitation of needing $[O_3]>[SO_2]$. In some embodiments, the $O_3$ filter allows for a direct measurement of $SO_2$ using the ECC approach described herein, without interference from $O_3$. In some further embodiments, the calibration and preparation procedures also described herein permit the retrieval of reliable and precise $SO_2$ measurements over a wide range of $SO_2$ concentrations as observable in the atmosphere.

In some embodiments, an $SO_2$ ECC makes a direct measurement of trace concentrations of $SO_2$ up to at least 10.6 mPa with a detection limit of about 1-2 ppb, and in some embodiments, further configurations are disclosed for measuring additional trace gases. In one embodiment a lightweight, balloon borne instrument that requires an electrochemical technique to measure $SO_2$ is disclosed.

In some embodiments a device or an instrument is disclosed, wherein the instrument effectively measures $SO_2$ in the field as compared with the dual $O_3/SO_2$ sonde approach of the prior art.

In some embodiments the instrument comprises an ozonesonde pump inlet filter, and in some embodiments removes >99% of ozone from the air being sampled by the ozonesonde pump. In some embodiments the ozonesonde pump inlet filter is designed to be used with the $SO_2$ ECC so that the sonde instrument measures only $SO_2$, removing in some embodiments, the need for adjusting the reported readings from the instrument for the ambient $O_3$ concentration.

In some embodiments the lightweight filter removes $O_3$ without impacting the concentration of $SO_2$, making it suitable for use on a $SO_2$ ECC, and in some embodiments allowing the sonde to make a direct measurement of $SO_2$. In some embodiments, the calibration, and operation procedures for the $SO_2$ ECC sonde provide step-by-step instructions for the preparation and calibration of the $SO_2$ ECC in the laboratory as part of the pre-flight procedures. In some embodiments, implementation of the calibration and operation procedures result in instrument performance consistent with the ozone measurement from the ozonesonde of the prior art, therefore in some embodiments the instrument disclosed herein comprises a maximum concentration (upper detection limit) of up to about 10.6 mPa, and a detection limit of about 1-2 ppb, along with a precision of about 7%.

In some embodiments a device for directly measuring trace gases is disclosed, wherein the device comprises: an electrochemical cell (ECC) (comprising a cathode wherein the EEC comprises a cathode solution; an anode, comprising an anode solution; an ion bridge connecting the cathode solution, and the anode solution; and circuitry, wherein the circuitry is configured to complete an electrical circuit between the anode and cathode); a sample intake structure, wherein the sample intake structure terminates in the cathode solution, and transfers an air sample from an environment to the cathode solution; a reference electrode, connected to the cathode; a battery, wherein the battery applies a voltage; and wherein the voltage is modulated by a voltage regulator, wherein the voltage regulator is connected in series to a resistor, and wherein the resistor is connected in series to the reference electrode. In some embodiments the reference electrode comprises platinum, in some other embodiments the cathode and the anode comprises platinum.

In another embodiment of the device, the sample intake structure further comprises an ozone $[O_3]$ filter. In some embodiments of the device the anode solution is potassium iodide (KI); in a further embodiment the cathode solution is potassium iodide (KI). In an embodiment of the device disclosed herein the trace gas is $SO_2$; and in a further embodiments the $SO_2$ is detectable at about 1-2 ppbv.

In another embodiment of the device disclosed herein the voltage is between 1 VDC AND 12 VDC, and in a further embodiment the voltage is about 12, 10, 7, 5, 4, 3.3, 3, 2, or 1 VDC, in a still further embodiment, the voltage is constant. In another embodiment the device described herein further comprises a radiosonde, wherein the radiosonde comprises a transmitter.

In some embodiments, a method for directly measuring trace gases is described herein, where the method comprises introducing an air sample into a cathode solution of the device described herein; passing a current through the resistor, and the reference electrode into the cathode solution, inducing an increase in electrical current in the cathode solution; measuring the increase in current; transmitting a signal proportional to the increase in current; receiving the signal; and calculating the amount of $SO_2$ in the air sample.

In another embodiment, a method for directly measuring trace gases is described herein, where the method comprises introducing an air sample into a cathode solution of an ECC sonde, wherein the sonde comprises: an electrochemical cell (ECC) wherein the ECC comprises: a cathode; a cathode solution; an anode; and an anode solution; a sample intake structure comprising an ozone filter; a reference electrode connected to the cathode; a battery, wherein the battery applies a voltage; a voltage regulator; and a resistor; applying a voltage from the battery; passing a current through the resistor and the reference electrode into the cathode solution; inducing an increase in electrical current in the cathode solution; measuring the increase in current; transmitting a signal proportional to the increase in current; receiving the signal and calculating the amount of $SO_2$ in the air sample. In another embodiment of the method, the reference electrode comprises platinum; in a further embodiment of the method the voltage is 12, 10, 7, 5, 4, 3.3, 3, 2, or 1 VDC. In one embodiment of the method disclosed herein the sample intake structure further comprises an ozone filter, and in a further embodiment transmitting is by a radiosonde transmitter. In another embodiment of the method the trace gas is $SO_2$, and in a further embodiment the $SO_2$ is detectable at about 1-2 ppbv. In some embodiments the ozone filter comprises a heater.

The foregoing has outlined rather broadly certain of the features of the exemplary embodiments of the present invention in order that the detailed description that follows may be better understood. It should be appreciated by those skilled in the art that the conception and the specific embodiments disclosed may be readily utilized as a basis for modifying or designing other methods and structures for carrying out the same purposes of the invention that is claimed below.

DETAILED DESCRIPTION OF DISCLOSED EXEMPLARY EMBODIMENTS

It should be understood at the outset that although an illustrative implementation of one or more embodiments are provided below, the disclosed systems and/or methods may be implemented using any number of techniques, whether currently known or in existence. The disclosure should in no way be limited to the illustrative implementations, drawings, and techniques below, including the exemplary designs and implementations illustrated and described herein, but may be modified within the scope of the appended claims along with their full scope of equivalents.

The following discussion is directed to various exemplary embodiments of the disclosure. One skilled in the art will understand that the following description has broad application, and the discussion of any embodiment is meant only to be exemplary of that embodiment, and that the scope of this disclosure, including the claims set out below, is not limited to that embodiment.

The drawing figures are not necessarily to scale. Certain features and components herein may be shown exaggerated in scale or in somewhat schematic form and some details of conventional elements may be omitted in interest of clarity and conciseness.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first component or device couples to a second, that connection may be through a direct engagement between the two components or devices, or through an indirect connection that is made via other intermediate devices and connections. As used herein, the term "about," when used in conjunction with a percentage or other numerical amount, means plus or minus 10% of that percentage or other numerical amount. For example, the term "about 80%," would encompass 80% plus or minus 8%. As used herein the terminology instrument, apparatus, device and sonde may be used interchangeably.

Overview

Disclosed herein are embodiments of methods of inducing a current in the cathode cell of an ECC ozone sonde which allows for the direct measurement of $SO_2$ independent of $O_3$.

Figure 2:
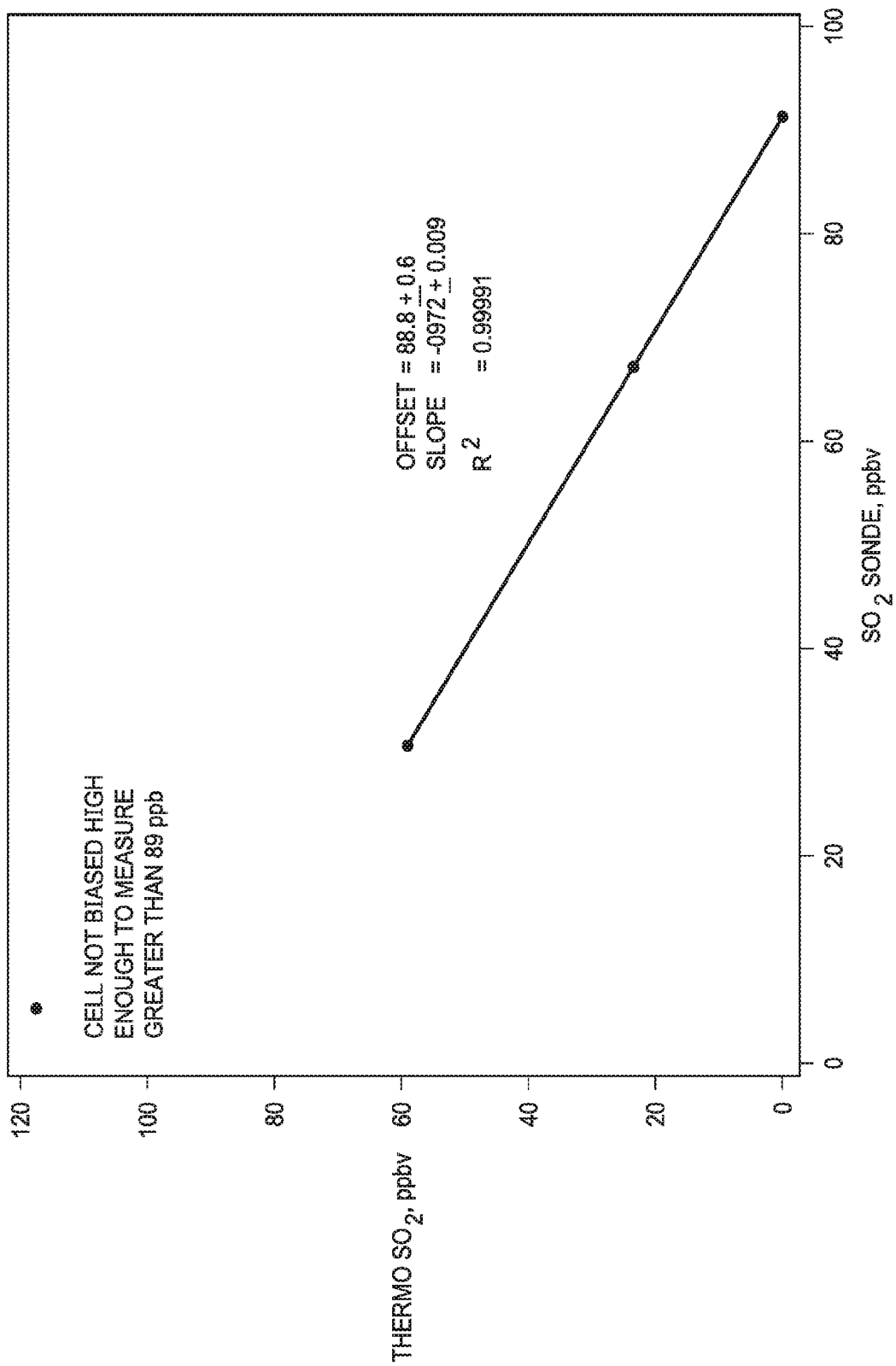
FIG. 2 illustrates the response of an $SO_2$ sonde with no ozone present compared to the response of a calibrated Thermo 43c-TL $SO_2$ instrument. Time period is a 1.5 hr. range at ~2:55-3:30 pm (as per FIG. 1). For the range of $SO_2$ less than the bias current, a linear response is observed.
Figure 3:
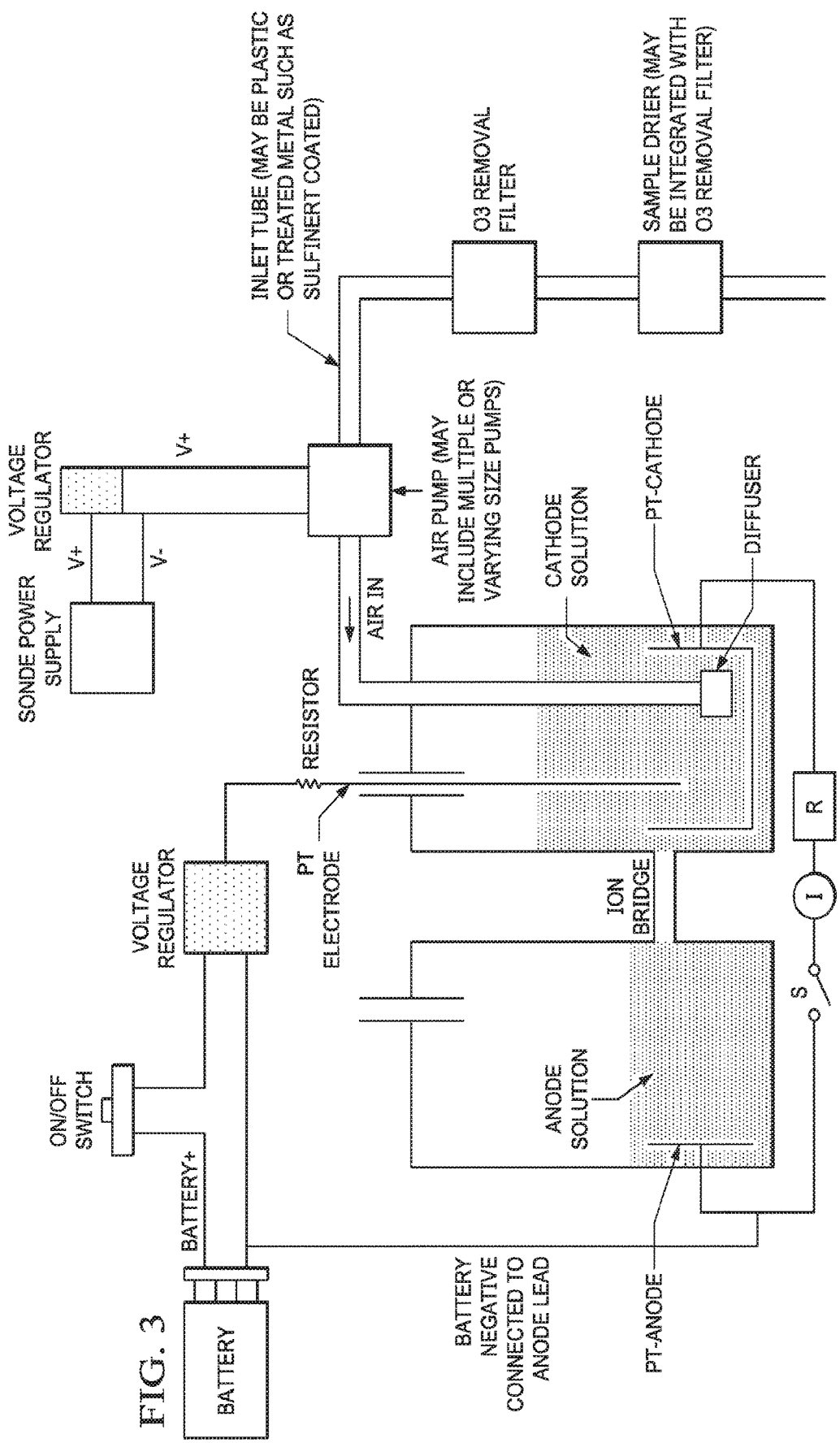
FIG. 3 illustrates an embodiment of an ECC sonde as disclosed herein.
Figure 4:
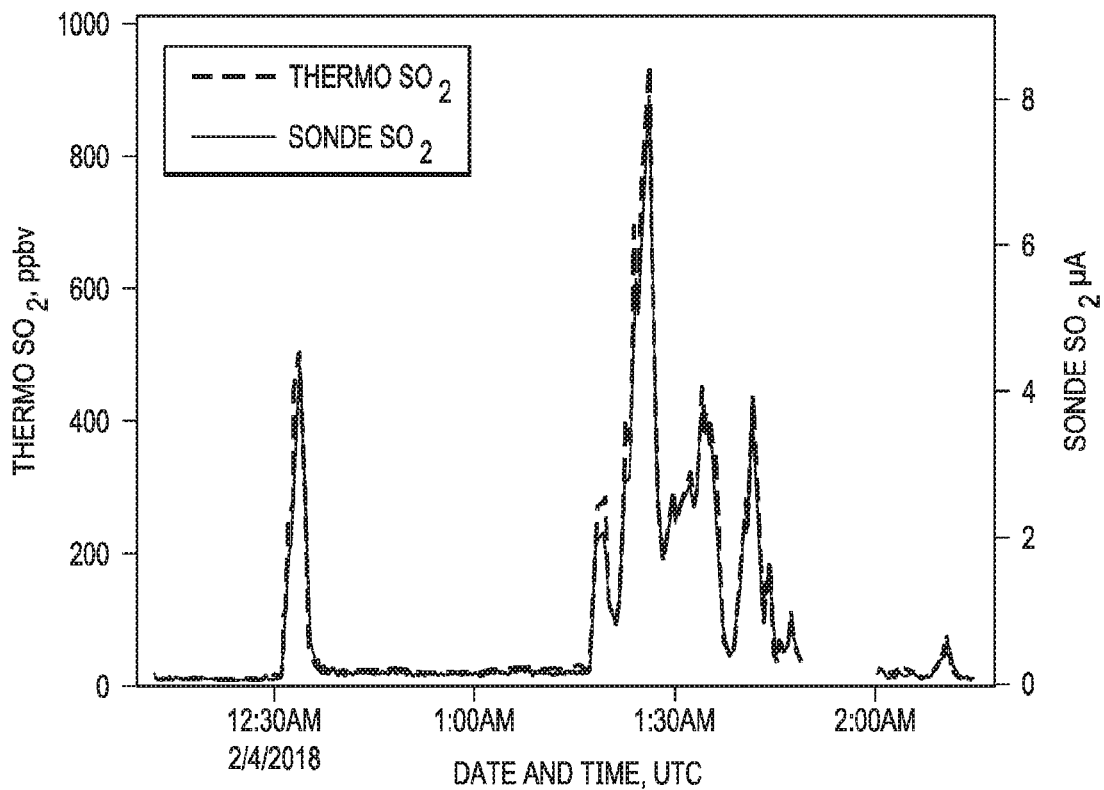
FIG. 4 illustrates a first measurement in the Kilauea plume (Hawaii), wherein the upper panel depicts a time series of a Thermo 43c-TL $SO_2$ analyzer (red, left axis) and the $SO_2$ sonde response (blue, right axis). The lower panel depicts a scatter plot of Thermo 43c-TL $SO_2$ analyzer (left axis) vs $SO_2$ sonde response (bottom axis). The $r^2$ value of 0.99276 indicates that the linear fit line explains 99.276% of the variation, indicative of a near perfect correlation between the Thermo 43c-TL $SO_2$ analyzer (of the prior art) and the $SO_2$ sonde response (an embodiment of the sonde disclosed herein). The Thermo Electron Corp. model 43c-TL as described and used throughout this disclosure is a pulsed fluorescence $SO_2$ analyzer intended to be used for laboratory testing as well as continuous monitoring of ambient air quality. In this work the 43c-TL analyzer is used as a reference standard to evaluate the performance of the new $SO_2$ sonde.
Figure 4:
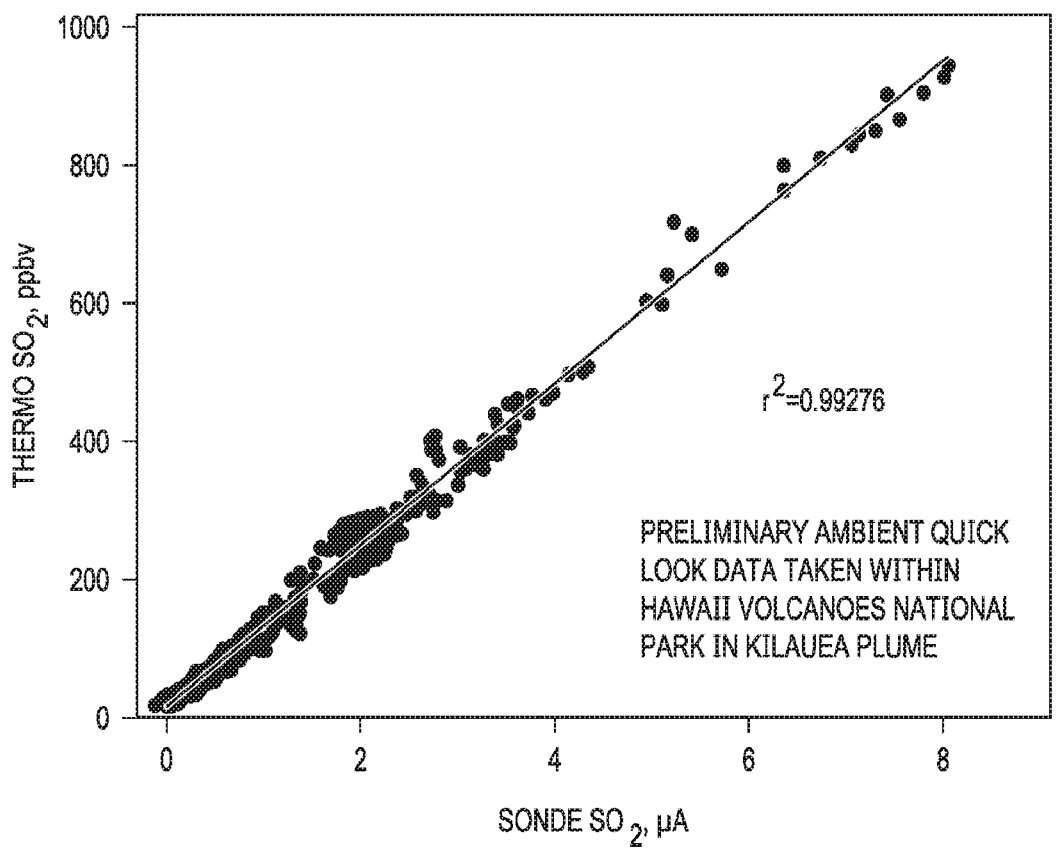
Figure 5:
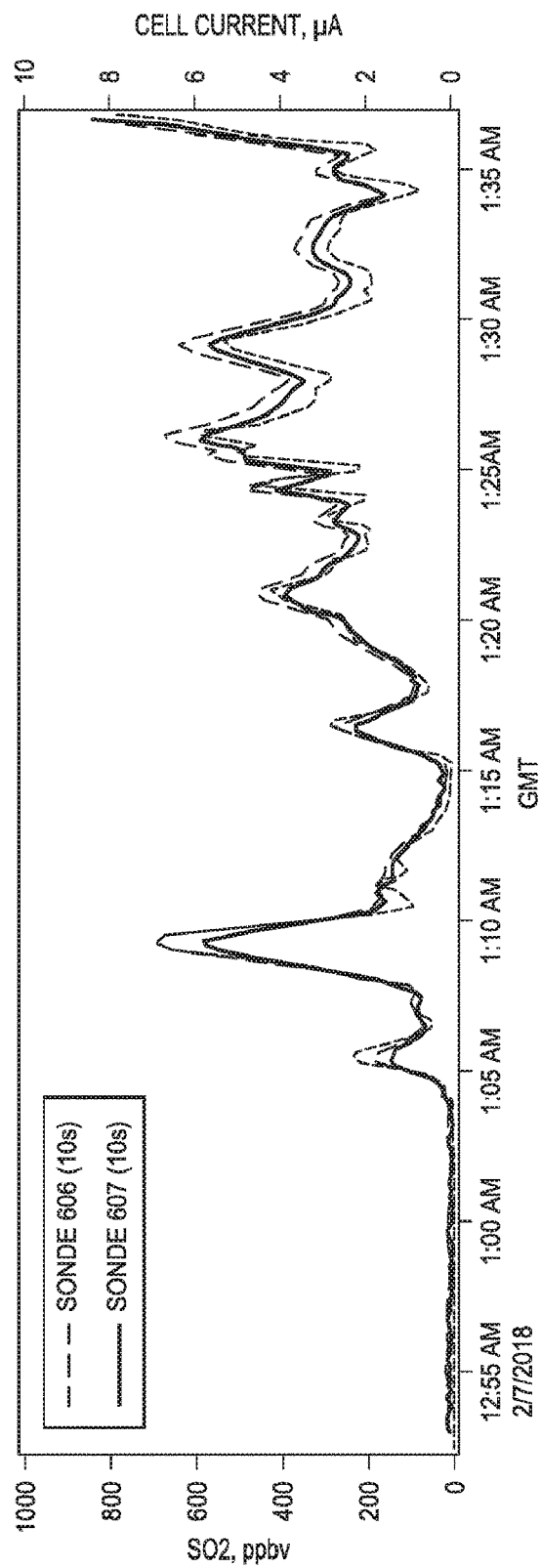
FIG. 5 illustrates a second set of measurements in Kilauea plume, wherein the upper panel depicts a time series of a Thermo 43c-TL $SO_2$ analyzer (red, left axis) and the $SO_2$ sonde response (blue and yellow, right axis); the lower panel depicts a scatter plot of Thermo 43c-TL $SO_2$ analyzer (left axis) vs $SO_2$ sonde response (bottom axis) for test sondes 607 and 606. The $r^2$ value of 0.93552 (607) and 0.955007 (606) indicates that the linear fit line explains 93.552% and 95.5007% of the variation, wherein each sonde independently provides a near perfect correlation with the Thermo 43c-TL $SO_2$ analyzer.
Figure 5:
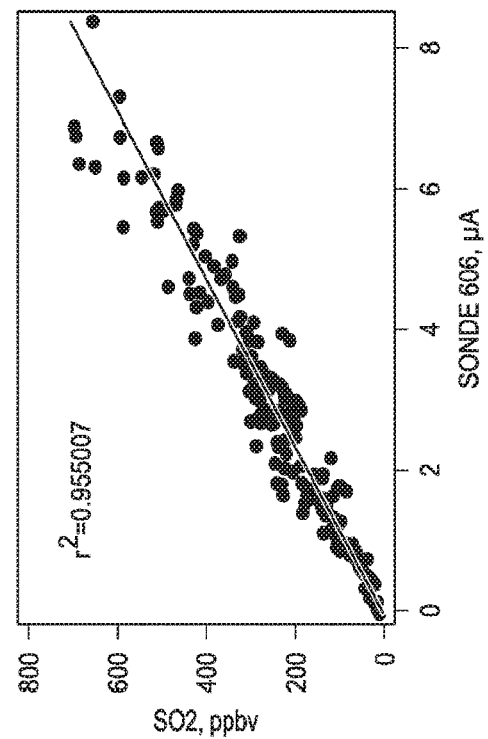
Figure 5:
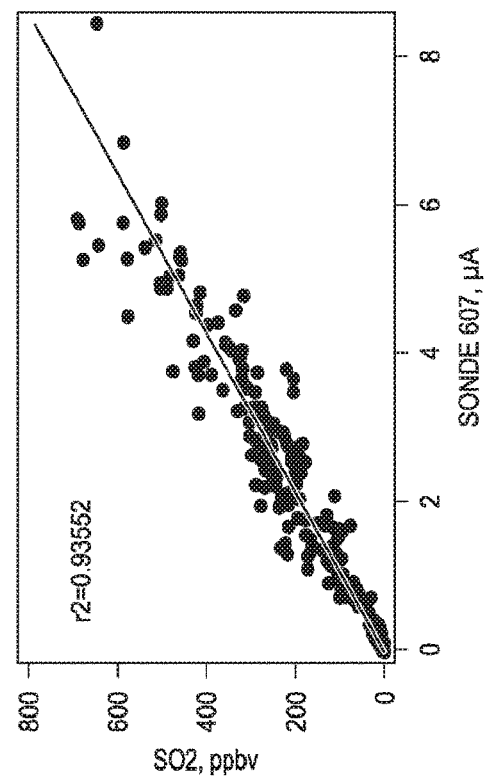
Figure 6:
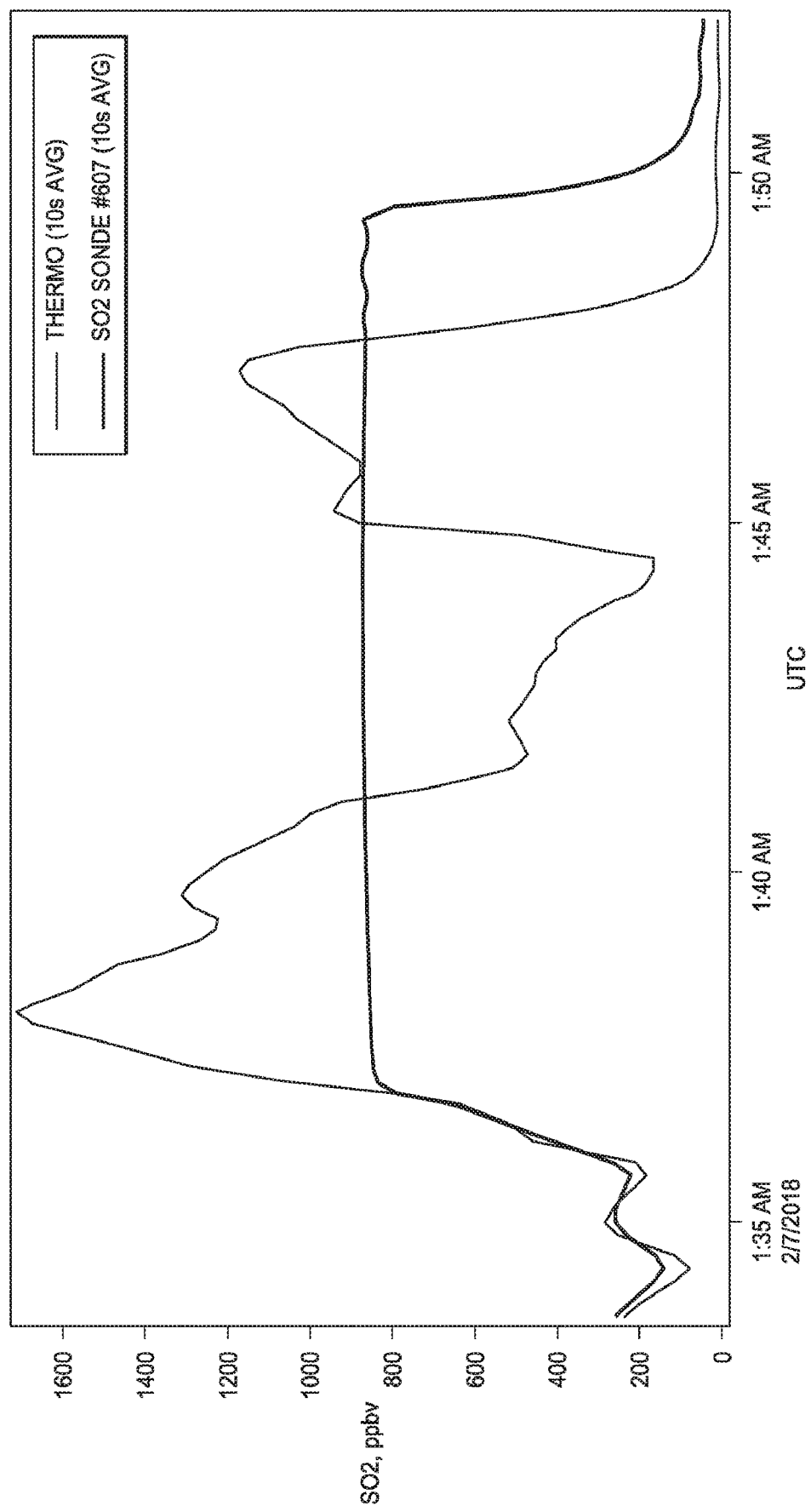
FIG. 6 depicts a time series showing Thermo 43c-TL and $SO_2$ sonde response in ppbv, wherein the Thermo 43c-TL trace provides a number of peaks, over the trace time. In this section of data the $SO_2$ sonde has saturated at it's maximum value (as indicated by the plateau of the lower trace), wherein the integral of the saturated (ambient $SO_2$ concentration that exceeds the upper limit of the $SO_2$ sonde) period, as indicated by the flat trace, on the $SO_2$ sonde is within 6-7% of the integral of the same period for the Thermo43c-TL. This allows reporting an integrated $SO_2$ measurement for comparison to column measurements in conditions when the sonde saturates.
Figure 7:
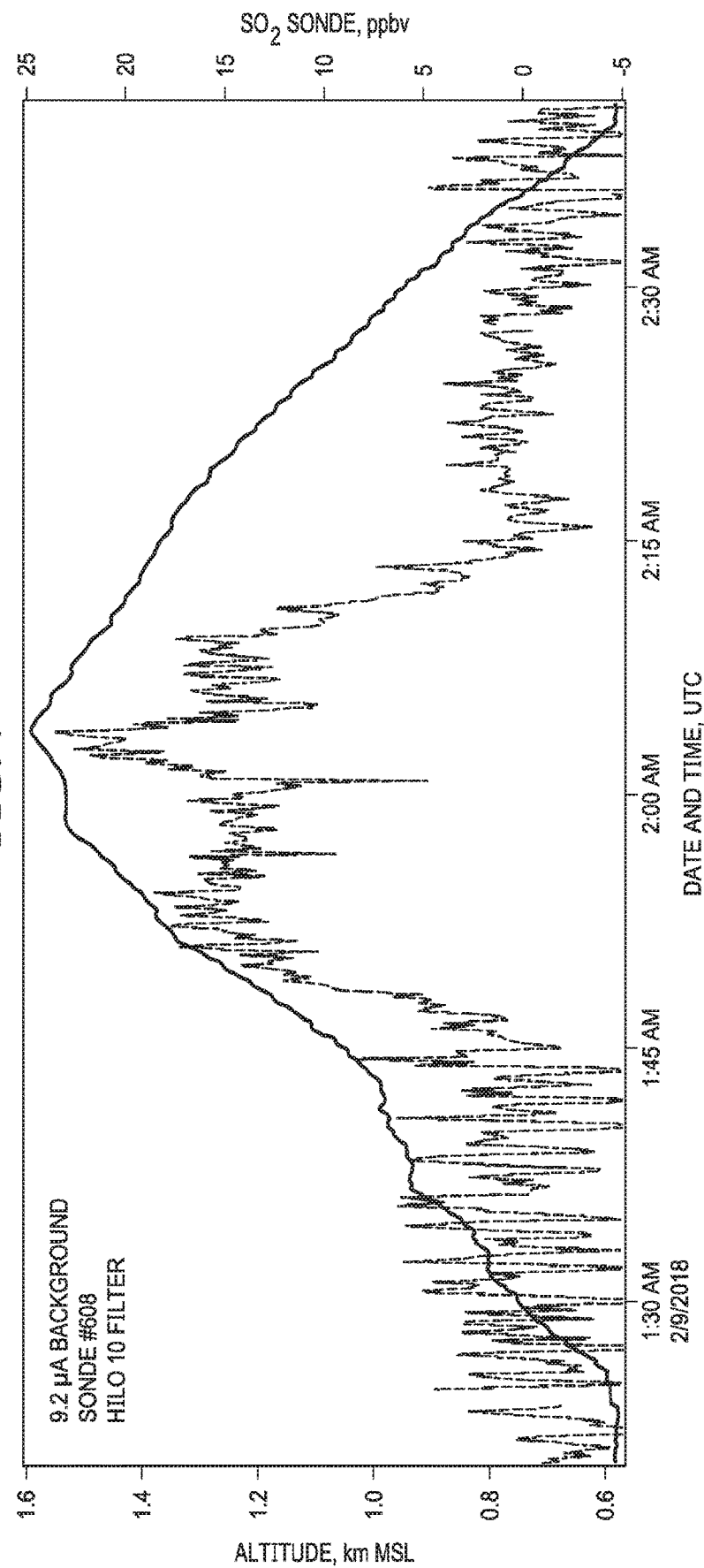
FIG. 7 depicts measurements of $SO_2$ from a tethered blimp flight up to 1 km above ground, wherein the results from the tethered blimp flight show a layer of $SO_2$ beginning about 400 meters above ground level on the ascent.
Figure 8:
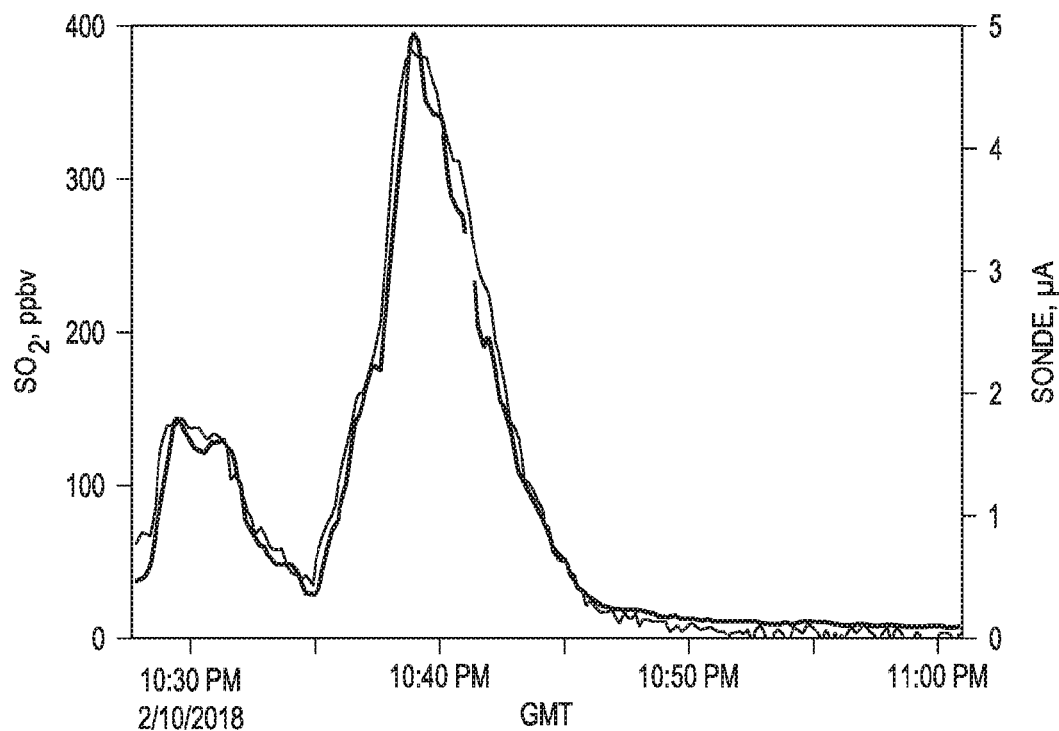
FIG. 8 depicts an additional ground measurement from a $SO_2$ sonde taken in the plume from Kilauea in Hawaii, wherein the upper panel depicts a time series of a Thermo 43c-TL $SO_2$ analyzer (left axis) and the $SO_2$ sonde response (right axis); the lower panel depicts a scatter plot of Thermo 43c-TL $SO_2$ analyzer (left axis) vs $SO_2$ sonde response (bottom axis). The $r^2$ value of 0.988641 indicates that there is near perfect correlation, between the Thermo 43c-TL $SO_2$ analyzer (of the prior art) and the $SO_2$ sonde response (an embodiment of a sonde herein disclosed).
Figure 8:
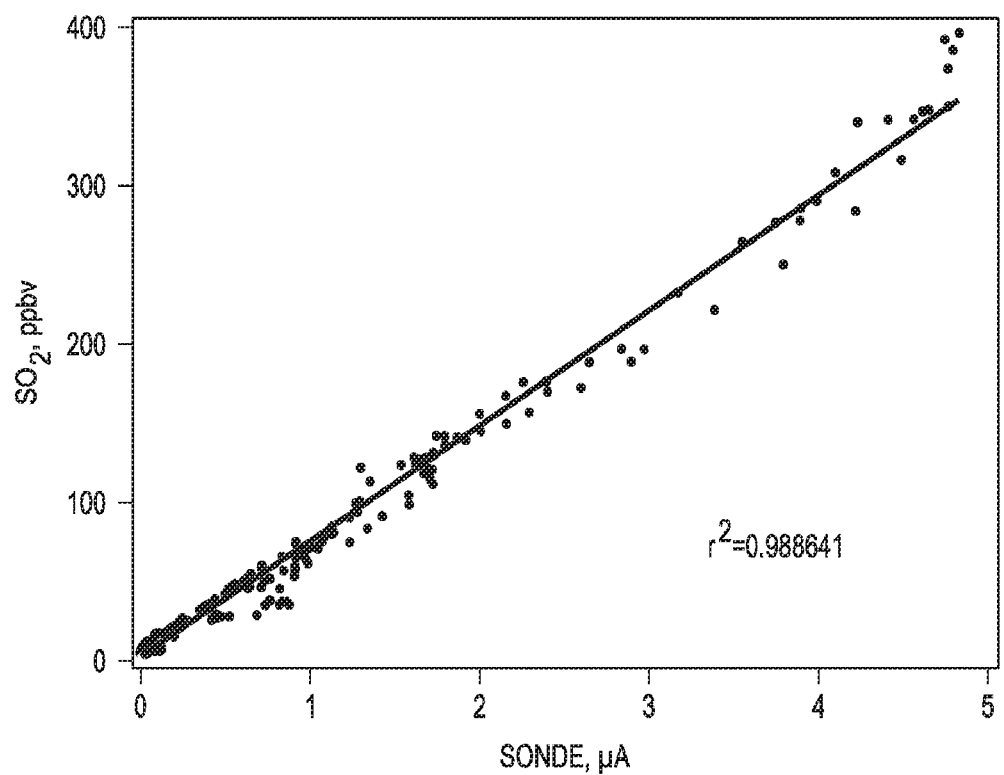
Figure 9:
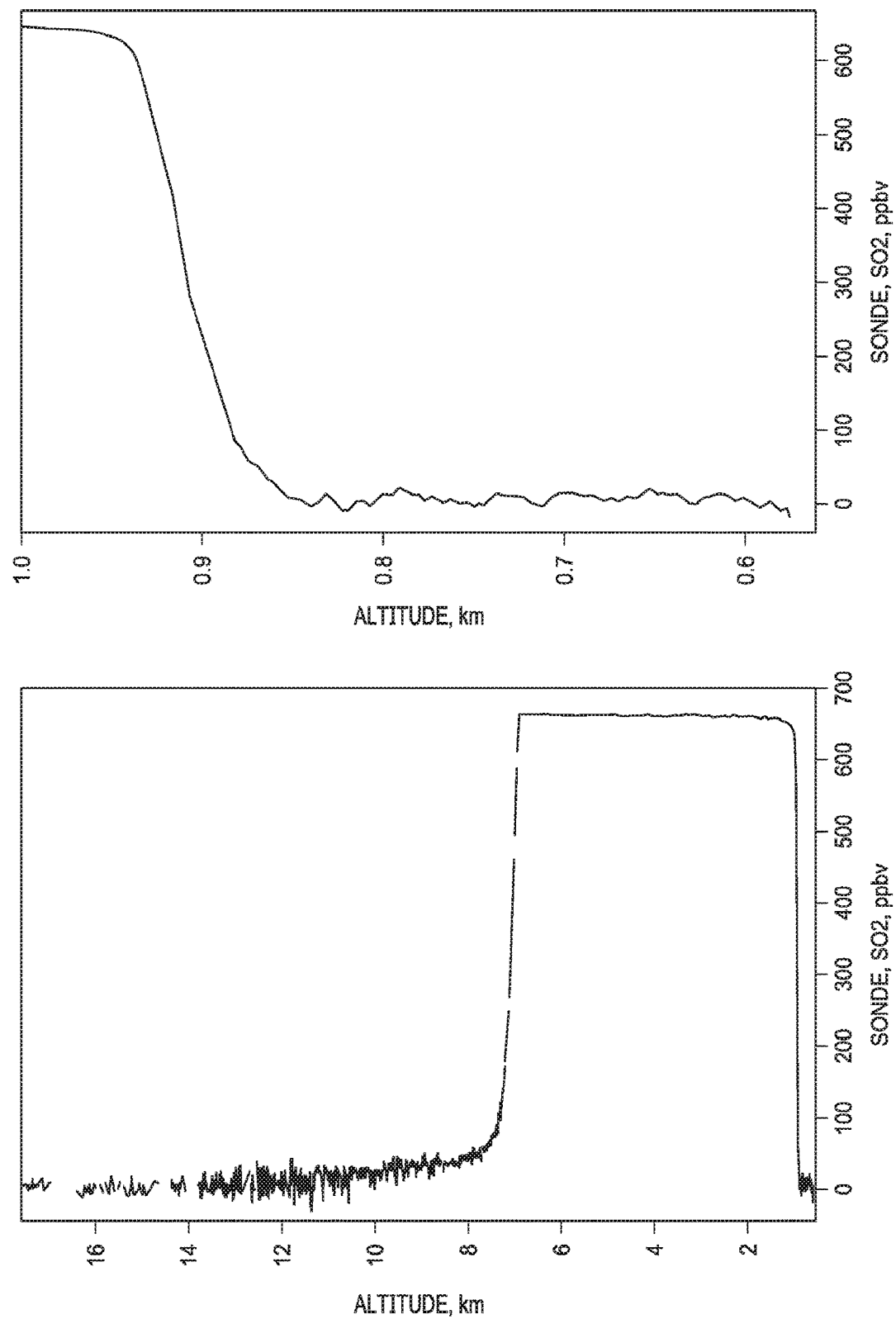
FIG. 9 depicts a plot of a $SO_2$ sonde flight data from the Kilauea plume (Hawaii), wherein the left panel depicts a vertical profile of the $SO_2$ sonde measurements (bottom axis) plotted against altitude above sea level (left axis). This indicates a very strong plume a few hundred meters above ground level (low layer of clouds and light rain washed the $SO_2$ out of the atmosphere at low levels, however above the clouds there was a strong $SO_2$ plume from Kilauea); the right panel depicts an expanded view of the lowest portion (up to 1 km) of the data from the left panel. This shows that the $SO_2$ sonde began to encounter the $SO_2$ plume around 280 m above the ground.

In this method, a standard ECC is modified by inserting a central platinum electrode into the cathode cell and applying a voltage modulated by a resistor connected in series with the electrode outside of the cathode cell. The platinum mesh at bottom of the ECC cathode cell that conducts the charge produced in the cathode cell is physically adjusted as necessary to provide sufficient clearance to avoid a short with the newly introduced central electrode so that the resulting current flows through the solution. The resulting "bias current" flowing in the cathode cell can be adjusted by appropriate selection of the introduced voltage and series resistor. Given the chemistry of the cathode cell, with this modification, the cell can now measure $[SO_2]>[O_3]$ as well as direct measurements of $[SO_2]$, unaffected by $O_3$, with the use of an appropriate ozone scrubber on the inlet of this modified ECC. Tests (illustrated in FIG. 1 and FIG. 2) have shown that this method of introducing a bias current in the cathode cell allows for the direct measurement of $SO_2$ with an accuracy and precision comparable to that of the standard $O_3$ sonde.

In some embodiments, platinum mesh from a recovered $O_3$ sonde wrapped around the cathode cell inlet tube was used as the central electrode. A strand of the mesh was pulled away from the mesh at one end to be used as a wire and routed through a slit in the exhaust tube of the cell. A current was applied to this wire to charge the solution.

In some embodiments platinum wire may be used as the central electrode. In some further embodiments, an external power supply and precision variable resistor may be used to generate and control the current.

In some embodiments for sondes to be flown, an onboard method of generating a current is needed. In one embodiment sonde pump batteries, and an appropriate resistor may be used.

While in some embodiments, the voltage of the current induced in the cell has no influence on the performance, the voltage from the batteries may change slightly during the flight and may affect the current induced in the cathode cell. The battery voltage is logged as part of the standard data set and may allow for the calculation of the bias current during processing.

In other embodiments, a voltage regulator to drop the battery voltage to a constant voltage such as 12, 5, or 3.3 VDC may be used, which is some embodiments may hold both the voltage and bias current constant. In some other embodiments, and to insure the functioning of the voltage regulator, adding this variable to the standard ECC data stream may require modifying both the sonde retrieval and post-flight processing software programs. These complications are avoided when the sonde battery voltage is part of the standard data stream. In the some embodiments a 0.5% KI solution in the cathode cells was for measurements of $O_3$. In some embodiments, the concentration of the KI in the cathode solution may be varied to determine if there is any sensitivity in the $SO_2$ measurement to the solution formulation as disclosed herein. Other solutions may be tested as methods of measuring other trace gases.

In some embodiments, the performance of the $SO_2$ sonde across a range of conditions (including simulated flights in a pressure chamber, the impact on the measurement of the inclusion of a sample filter intended to remove volcanic ash) and the performance and impact of a filter designed to remove $O_3$ without impacting $SO_2$ based on materials suggested as part of the design of the dual $SO_2$ may be optimized.

In other embodiments, pressure chamber tests may verify the expected performance at reduced pressures encountered in flight so that an accurate determination of the sensitivity and detection limits at altitudes at which influence of a tropical, explosive volcanic eruption might inject $SO_2$ into the upper atmosphere (as last occurred with the eruption of Mt. Pinatubo in 1991) may be assessed.

In some embodiments, a 50 mm Teflon sample filter media may be tested for exposure to the volcanic ash with varying sample loadings to bracket the conditions expected to be seen in sonde flights after a volcanic eruption.

These tests, along with additional analysis of previous dual-sonde launches without particle filters, may determine if a particle filter is desirable, and if so, what impact aerosol loadings on the filters may have on measured $SO_2$ and/or $O_3$ readings. In some embodiments, in order to make the $SO_2$ sonde responsive only to $SO_2$, an $O_3$ scrubbing filter for the intake of the $SO_2$ sonde may be implemented. This filter must be selective in only removing $O_3$ and allowing $SO_2$ to be transmitted at ~100% efficiency.

In some embodiments, a filter design that employs a shredded natural rubber fiber may be used. In other embodiments, additional materials may be used. By removing $O_3$ from the sample air, in some embodiments the interference from $O_3$ in the $SO_2$ sonde measurement may be eliminated, thereby removing the need to launch two sondes to measure $SO_2$ profiles, thus allowing for a "clean" measurement of $SO_2$. In some further embodiments, it may be desirable to launch an $O_3$ sonde in conjunction with the $SO_2$ sonde to collect both profiles simultaneously. In some embodiments, by installing a $SO_2$ filter on the $O_3$ sonde and an $O_3$ filter on the $SO_2$ sonde, it may be possible to collect interference-free profiles of both $SO_2$ and $O_3$. Field tests may be conducted in volcanic plumes where both $SO_2$ and ash are regularly emitted.

The test atmospheres in the field may be generated by a commercially available $O_3$ generator, and $SO_2$ permeation tube. In some embodiments, establishing a robust yet portable calibration protocol may be implemented for responding rapidly to remote locations after a volcanic eruption, and allowing deployment of the system to the field quickly to capture the plume within a few days of eruption.

In some further embodiments, precise emission rates from permeation tubes may provide stable calibration sources in the lab, but the realities of field work, especially for rapidly deployed systems, can lead to variable emission rates as the storage and operating temperatures and access to precision scales for weighing may be hard to control as well as in the laboratory environment. Therefore, in some embodiments and to overcome this limitation, the actual mixing ratio of the test atmosphere may be determined by the calibrated $O_3$ and $SO_2$ instruments. This approach eliminates the need for precision control of the permeation tube.

In other embodiments, the $SO_2$ instrument may include an internal permeation oven. The output of the permeation oven and $O_3$ generator may be combined in a Teflon mixing volume and the resulting mixture may be sampled by all sondes being launched as well as the calibrated instruments. Comparison of the sonde responses to that of the instruments may verify sonde accuracy prior to launch. These instruments and the associated components (i.e., data acquisition and zero air generator) may be packaged in a rackmount shipping case to make shipping a complete field system easier, thereby improving transportation, and logistics.

In some embodiments three sondes may be launched on each payload. Two sondes may be used in the current deployed dual-sonde configuration and the third may employ the new direct $SO_2$ measurement sonde method.

Disclosed herein, in some embodiments is a technique to modify a standard ECC $O_3$ sonde to be used as a sonde for direct measurements of $SO_2$ and potentially other trace gases; in a further embodiment, an inlet scrubber to selectively remove $O_3$ and other trace gases, as needed, from the sample, and in a still further embodiment, an operating procedure for using the sonde in laboratory and field sites.

Data produced from experiments described herein include: 1. the precision and accuracy of the $SO_2$ sonde measurement based on laboratory tests at a range of pressures from the surface to the lower stratosphere; 2. the agreement between the dual sonde $SO_2$ measurement and that of the new $SO_2$ sonde in the troposphere; 3. the effectiveness of the $O_3$ filter in scrubbing ozone; 4. the sensitivity of the $SO_2$ measurement to the cathode solution formulation, including a recommendation for the best solution to use, and 5. the effectiveness of the aerosol filter and its impact on the $SO_2$ measurement.

Examples

In some embodiments a sonde as disclosed herein, may comprise a 9 v battery which is separated from the instrument's primary power source by a voltage regulator. In some embodiments a 5 VDC voltage is applied, in other embodiments the voltage is between 1 VDC and 10 VDC, and in some embodiments the voltage is held constant. In some further embodiments the voltage is 9, 8, 7, 6, 5, 4, 3, 2, OR 1 VDC, or partial numbers thereof. A positive current is passed through a resistor (which can set the maximum cell bias (determining the upper limit of detection) to a desirable measurement range (determined by the upper and lower detection limits required for the experiment)), and into a cathode solution via a fine platinum wire which comprises the electrode. The negative lead from the battery/voltage regulator is connected to the anode at a circuit board. An electrical current is induced by the electrode in the cathode solution. The electrical current effectively "adds" a signal that is then measured by the circuitry of the apparatus. The signal (data) is transmitted via an attached radiosonde's transmitter and received by an antenna/receiver/computer station on the ground. As such the concentration of $SO_2$ or other trace gases are measured remotely at a specific altitude.

In some embodiments, the addition of an external on-off means, wherein the means may comprise a switch or a plug-in connector may be provided, such that the sonde can be fully packaged within a closed environment, and subsequently started at a later time.

In other embodiments of the sonde described herein, the ability to change pump speed to adjust the sensitivity, and therefore upper and lower detection limits, of the sonde is provided. Increasing pumping speed by the adding one or more extra pumps can increase sensitivity (less ppbv $SO_2$ per uA) and thereby reduce the lower detection limit. Further, in some embodiments, the addition of a voltage regulator inline with the pump may slow the speed, and reducing the sensitivity (more ppbv $SO_2$ per uA), and effectively increasing the upper detection limit. Thus, depending on the usage or environment of detection, the sonde may be calibrated for lower detection limits of $SO_2$ (stratospheric measurements) or higher upper limits of $SO_2$ (near source measurements such as in the proximity of a source of $SO_2$ (i.e. active volcano, industrial facility, power plant, etc.). Thus in some embodiments, the selection of current to be applied to the cell also has a large effect on both upper and lower detection limits. This is achieved by changing the resistor(s) between the voltage regulator and platinum electrode.

In some further embodiments the addition of a diffuser to the end of the bubbler tube—may make the bubbles of the atmospheric sample smaller relative to the bubbles formed without the diffuser present, and create a greater uniformity in the bubble size. The smaller bubbles will increase $SO_2$ uptake into the solutions and increase sensitivity (less ppbv SO2 per uA) of the sonde. Additionally, uniform bubbles reduce system noise and therefore reduce the lower end detection limit, making the system more sensitive.

In some embodiments the use of tubing that is optimized for gas delivery systems, lower pressures, and Inert applications may be used for the ECC sonde inlet as disclosed herein, and in order to increase response time (low to high $SO_2$) and reduce hysteresis (high to low $SO_2$) relative to standard teflon/plastic inlet tube. Such tubing is also useful in analyzing for parts-per-billion levels of organosulfur compounds. (See for example Sulfinert tubing at www.restek.com).

In some embodiments, the addition of a sample-drying approach to the sonde may reduce humidity effects on $SO_2$ transmission efficiency of the treated filter. This may be achieved in some embodiments, by heating the filter and/or filter assembly, or in some further embodiments by adding a sample drier before the filter. In some other embodiments, test solutions may be utilized with improved hysteresis. In some embodiments, such solutions include changing the ratios of iodide compounds and buffer in the solutions.

In other embodiments an ECC sonde of the present invention is localized at the desired location at which sample collection is required by balloon. In other embodiments the ECC sonde disclosed herein is disposable.

While the preferred embodiments have been shown and described, modifications thereof can be made by one skilled in the art without departing from the spirit and teachings of the invention. The embodiments described herein are exemplary and representative, and are not intended to be limiting. Many variations and modifications of the invention disclosed herein are possible and are within the scope of the invention. Accordingly, the scope of protection is not limited by the description set out above, but is only limited by the claims which follow, that scope including all equivalents of the subject matter of the claims.

All patents, patent applications and publications cited herein and below, are hereby incorporated herein by reference to the extent that they provide materials, methods and explanatory details supplementary to those set forth herein: U.S. Pat. No. 3,681,228; Electrochemical concentration cells for gas analysis, Annales De Geophysique, 25(1), 203-210; Komhyr, W. D., B. J.; Connor, I. S. McDermid, T. J. McGee, A. D. Parrish, and J. J. Margitan (1995), Comparison of STOIC 1989 ground-based lidar, microwave spectrometer, and dobson spectrophotometer Umkehr ozone profiles with ozone profiles from balloon-borne electrochemical concentration cell ozonesondes, Journal of Geophysical Research-Atmospheres, 100(D5), 9273-9282; Morris, G. A., W. 3: D. Komhyr, J. Hirokawa, J. Flynn, B. Lefer, N. Krotkov, and F. Ngan (2010), A Balloon Sounding Technique for Measuring $SO_2$ Plumes, Journal of Atmospheric and Oceanic Technology, 27(8), 1318-1330, doi: 10.1175/2010jtecha1436.1.Komhyr, W. D. (1969), Electrochemical concentration cells for gas analysis, Annales De Geophysique, 25(1), 203-210; and Smit, H. G. J., et al. (2007), Assessment of the performance of ECC-ozonesondes under quasi-flight conditions in the environmental simulation chamber: Insights from the Juelich Ozone Sonde Intercomparison Experiment (JOSIE), Journal of Geophysical Research-Atmospheres, 112(D19), doi:D1930610.1029/2006jd007308.

What is claimed is:

1. A device for measuring atmospheric trace gases comprising:
    an electrochemical cell (ECC) comprising:
        a cathode in a cathode solution;
        an anode in an anode solution;
        an ion bridge connecting said cathode solution, and said anode solution; and
        circuitry, wherein said circuitry is configured to complete an electrical circuit between said anode and cathode;
    a sample intake structure, wherein said sample intake structure terminates in said cathode solution, and transfers an air sample comprising $SO_2$ from an atmospheric environment to the cathode solution, wherein said sample intake structure comprises an ozone filter that selectively removes $O_3$ from the air sample while transmitting the $SO_2$;
    a central electrode, in contact with said cathode solution;
    a battery, wherein the battery applies a voltage; and wherein the voltage is modulated by a voltage regulator, wherein the voltage regulator is connected in series to a resistor, and wherein the resistor is connected in series to said central electrode.

2. The device of claim 1, wherein the central electrode comprises platinum.

3. The device of claim 1, wherein the cathode and the anode comprises platinum.

4. The device of claim 1, wherein the anode solution is potassium iodide (KI).

5. The device of claim 1, wherein the cathode solution is potassium iodide (KI).

6. The device of claim 1, further comprising a sample drier before the $O_3$ filter.

7. The device of claim 6, wherein the $SO_2$ is detectable at 1-2 ppbv.

8. The device of claim 1, wherein the voltage is between 1 VDC AND 12 VDC.

9. The device of claim 8 wherein the voltage is 12, 5, or 3.3 VDC.

10. The device of claim 8, wherein the voltage is constant.

11. The device of claim 1 further comprising a radiosonde, wherein the radiosonde comprises a transmitter.

12. A method for measuring atmospheric trace gases comprising:
    introducing an air sample into a cathode solution of the device of claim 1;
    passing a current through the resistor, and the central electrode into the cathode solution,
    inducing an increase in electrical current in said cathode solution;
    measuring the increase in current;
    transmitting a signal proportional to the increase in current;
    receiving the signal; and
    calculating the amount of $SO_2$ in said air sample.

13. The device of claim 1, wherein the $O_3$ filter removes more than 99% of the $O_3$ in the air sample.

14. A method for measuring trace gases comprising:
    introducing an air sample into a cathode solution of an ECC sonde, wherein the sonde comprises:
        an electrochemical cell (ECC) wherein said ECC comprises:

a cathode;
a cathode solution;
an anode; and
an anode solution;
a sample intake structure comprising an ozone filter that selectively removes $O_3$ from the air sample while transmitting the $SO_2$;
a central electrode connected to said cathode;
a battery, wherein the battery applies a voltage;
a voltage regulator; and a resistor;
applying a voltage from the battery passing a current through the resistor and the central electrode into the cathode solution;
inducing an increase in electrical current in said cathode solution;
measuring the increase in current;
transmitting a signal proportional to the increase in current;
receiving the signal; and
calculating the amount of $SO_2$ trace gas in said air sample.

15. The method of claim 14, wherein the central electrode comprises platinum.

16. The method of claim 15, wherein the voltage is 12, 5, or 3.3 VDC.

17. The method of claim 16, wherein the ozone filter comprises shredded natural rubber fiber.

18. The method of claim 17, wherein introducing further comprises heating said air sample.

19. The method of claim 14, wherein the transmitting is by a radiosonde transmitter.

20. The method of claim 14, wherein the $O_3$ filter removes more than 99% of the $O_3$ in the air sample.

\* \* \* \* \*